(12) United States Patent
Lin

(10) Patent No.: US 8,820,538 B1
(45) Date of Patent: Sep. 2, 2014

(54) METHOD AND APPARATUS FOR PARTICLE SORTING

(71) Applicant: Namocell LLC, Palo Alto, CA (US)

(72) Inventor: Junyu Lin, Palo Alto, CA (US)

(73) Assignee: Namocell LLC, Palo Alto, CA (US)

( * ) Notice: Subject to any disclaimer, the term of this patent is extended or adjusted under 35 U.S.C. 154(b) by 0 days.

(21) Appl. No.: 14/216,185

(22) Filed: Mar. 17, 2014

(51) Int. Cl.
*B07C 5/00* (2006.01)
*B03B 5/00* (2006.01)

(52) U.S. Cl.
CPC .................................. *B03B 5/00* (2013.01)
USPC ........................... 209/552; 209/586; 422/504

(58) Field of Classification Search
USPC ......... 209/210, 552, 576–577, 586–588, 932; 422/502–504
See application file for complete search history.

(56) References Cited

U.S. PATENT DOCUMENTS

| | | | |
|---|---|---|---|
| 3,710,933 A | 1/1973 | Fulwyler et al. | |
| 4,175,662 A | 11/1979 | Zold | |
| 5,489,506 A | 2/1996 | Crane | |
| 5,750,015 A * | 5/1998 | Soane et al. | 204/454 |
| 5,837,200 A | 11/1998 | Diessel et al. | |
| 5,968,820 A | 10/1999 | Zborowski et al. | |
| 6,120,735 A | 9/2000 | Zborowski et al. | |
| 7,160,730 B2 | 1/2007 | Bach et al. | |
| 7,392,908 B2 | 7/2008 | Frazier | |
| 7,425,253 B2 | 9/2008 | Voldman et al. | |
| 7,428,971 B2 | 9/2008 | Hirano et al. | |
| 7,452,725 B2 * | 11/2008 | Leary et al. | 436/63 |
| 7,745,221 B2 | 6/2010 | Butler et al. | |
| 7,807,454 B2 | 10/2010 | Oh et al. | |
| 7,820,427 B2 * | 10/2010 | Unger et al. | 435/286.5 |
| 8,349,277 B2 * | 1/2013 | Azimi et al. | 422/507 |
| 8,387,803 B2 | 3/2013 | Thorslund et al. | |
| 8,567,608 B2 * | 10/2013 | Deshpande et al. | 209/552 |
| 2004/0233424 A1 * | 11/2004 | Lee et al. | 356/246 |
| 2006/0177348 A1 * | 8/2006 | Yasuda et al. | 422/73 |
| 2007/0178582 A1 * | 8/2007 | Koser | 435/288.5 |
| 2008/0138010 A1 | 6/2008 | Dou et al. | |
| 2008/0213821 A1 * | 9/2008 | Liu et al. | 435/39 |
| 2011/0030808 A1 | 2/2011 | Chiou et al. | |
| 2012/0103817 A1 | 5/2012 | Omori et al. | |
| 2013/0192958 A1 | 8/2013 | Ding et al. | |
| 2014/0087412 A1 * | 3/2014 | Fouras et al. | 435/29 |

OTHER PUBLICATIONS

Perkin Elmer; FlexDrip PLUS Precision Reagent Dispenser (product information); 4 pgs.; © 2007 (year of pub. sufficiently earlier than effective US filed and any foreign priority date).

* cited by examiner

*Primary Examiner* — Joseph C Rodriguez
(74) *Attorney, Agent, or Firm* — Shay Glenn LLP

(57) ABSTRACT

Apparatus and methods for sorting and dispensing microparticles using a flow switch mechanism wherein changing flow rate into the flow switch changes flow path. The present invention is well-suited for precisely sorting microparticles, such as cells, for applications such as cell line development, monoclonal antibody selection and single cell research, etc.

30 Claims, 4 Drawing Sheets

METHOD AND APPARATUS FOR PARTICLE SORTING

CROSS REFERENCE TO RELATED APPLICATIONS

None.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Described herein are apparatus (devices and systems) and methods for automatically sorting and dispensing microparticles, such as single cells. These techniques may be particularly useful for biological and medical applications.

BACKGROUND

Flow cytometry is used to differentiate various types of cells and other similar small particles. Conventional flow cytometers commonly comprise an optically-transparent flow cell, usually made of quartz, having a central channel through which a stream of cells to be individually identified is made to flow. Movement of the cell stream through the flow cell channel is hydrodynamically entrained to the central longitudinal axis of the flow cell channel by a cell-free sheath liquid that concentrically surrounds the cell stream and flows along with the cell stream as it passes through the flow cell channel. As each cell passes through a cell-interrogation zone of the flow cell channel, it is irradiated with a focused beam of radiation (e.g., laser). Upon impinging upon each cell, the laser beam is scattered in a pattern characteristic of the morphology, density, refractive index and size of the cell. Further, the spectral characteristics of the laser beam may act to excite certain fluorochromes associated with selected cells, as may be the case when a cell's DNA has been previously stained with such fluorochromes, or when a fluorochrome molecule has been conjugated with a selected type of cell, either directly or via an intermediate. Photodetectors strategically positioned about the optical flow cell serve to convert the light-scattered by each cell and the fluorescence emitted by the excited fluorochromes to electrical signals which, when suitably processed, serve to identify the irradiated cell. In addition to the light scatter and fluorescence measurements made on each cell, some flow cytometers further characterize each cell by measuring certain physical and/or electrical properties of each cell as it passes through the flow cell. The cells may be sorted to selectively remove and collect certain cells of interest (e.g., abnormal cells) from the cells that have already passed through the optical flow cell and have been identified. Various sorting techniques have been developed, including methods requiring forming and deflecting droplets containing one or a small number of cells.

For example, a cell-sorting component may include a piezoelectric device that acts to vibrate the flow cell so as to effect the production a stream of droplets from the cell-entraining sheath liquid exiting from the flow cell. Ideally, each droplet contains but a single cell that has been characterized as to cell type by the light-scatter and fluorescence measurements just made on such cell. Each droplet in the droplet stream is then electrostatically charged as it passes between a pair of electrically charged plates, and each charged droplet is selectively deflected (or not deflected) towards a collection container as it passes between a pair of electrostatically charged deflection plates, such plates being charged to a droplet-deflecting polarity only at a time to deflect droplets (and cells) of interest. The instantaneous polarity of the deflection plates is determined by a cell-characterization processor that processes the cell-measurement signals from the optical flow cell.

Such sorting of microparticles such as cells is very important in biological research and medical applications. One of the first cell sorting apparatus was invented by Mack Fulwyler (e.g., U.S. Pat. No. 3,710,933). In his invention, tiny liquid droplets were sorted by electrostatic force. Most commercial cell sorters are still based on this technique, however other methods of cell sorting have been invented. Cells can be sorted by physical defection of cell stream, such as deflecting cell stream to desired channel with gas impulse (e.g., U.S. Pat. No. 4,175,662, U.S. Patent Application Publication No. 2011/0030808), by impulsive hydraulic force created by piezoelectric beam (U.S. Pat. No. 7,392,908), or by magnetostrictive gates (U.S. Pat. No. 7,160,730). Cells can also be sorted by manipulating single cells in micro-fabricated channels by optical force (U.S. Pat. No. 8,426,209, U.S. Pat. No. 7,745,221, U.S. Pat. No. 7,428,971, U.S. Patent Application Publication No. 2008/0138010), by acoustic force (U.S. Pat. No. 8,387,803, U.S. Patent Application Publication No. 2013/0192958, U.S. Patent Application Publication No. 2012/0160746), by magnetic force (U.S. Pat. No. 8,071,054, U.S. Pat. No. 7,807,454, U.S. Pat. No. 6,120,735, U.S. Pat. No. 5,968,820, U.S. Pat. No. 5,837,200), or by dielectrophoretic force (U.S. Pat. No. 8,454,813, U.S. Pat. No. 7,425,253, U.S. Pat. No. 5,489,506, U.S. Patent Application Publication No. 2012/0103817). All of these methods typically involve complex fluidic systems and sophisticated electrical control systems, which make cell sorting apparatus expensive to build, and difficult to use.

In addition, the vast majority of known cell sorting mechanisms are focused on the sorting mixed cells into two or more populations. Droplet sorting by electrostatic force as described in U.S. Pat. No. 3,710,933 is the preferred mechanisms to deliver sorted individual cell to a predetermined location in real time. Unfortunately, droplet sorting is typically limited to delivery of sorted individual cells to a relative large area (e.g., more than 5 mm in diameter); for areas smaller than 5 mm in diameter, the deliver accuracy becomes very low because droplets typically travel at speed more than 1 m/s and to aim the droplets precisely to an area less 5 mm in diameter (e.g., using electrostatic force) is very difficult, particularly the speed of droplet is not constant. For example, currently available droplet cell sorters, such as BD ARIA III can sort individual cells directly into 96-well cell culture plate, in which the area of each well is about 6.5 mm in diameter, with accuracy of 70%. However, sorting individual cell into 384-well cell culture plate which is about 3 mm in diameter is not practical.

In contrast, there are commercially available technologies for delivering small volumes of liquids to precise locations. For example, the FLEXDROP (Perkin Elmer) is a liquid dispenser capable of delivering small amounts of liquid to a precise location having an area of less than 1 mm in diameter. Unfortunately, such liquid dispensers cannot sort cells.

Thus, it would be beneficial to provide a microparticle sorter that can address the problems discussed above. In particular, it would be beneficial to provide methods and apparatus that are capable of automatically sorting microparticles (e.g., individual cells or small groups of cells in a liquid suspension) and delivering them in small volumes of liquid to small diameter wells. Described herein are apparatus and methods capable of easily, inexpensively and efficiently sorting microparticles.

SUMMARY OF THE DISCLOSURE

In general, described herein are apparatus (e.g., systems and devices) and methods for sorting microparticles for effectively and precisely sorting and dispensing individual microparticles, such as a single cell or small group of cells, to a very small area. These methods and apparatus do not require complex fluidic and control systems. In particular, described herein are flow switches that may be used to differentially sorting microparticles based on the flow rate of the microparticle and/or the flow rate of the fluid surrounding the microparticle. These flow switches differentially directs a fluid flowing through the flow switch based on the flow rate of the fluid. Further, these flow switches may be used in conjunction with an identification and control module which can determine when a microparticle having predetermined properties is within the flow switch, and can increase (or decrease) the flow rate of the fluid carrying the microparticle to sort the microparticle. As used herein, a flow switch is a switch that sorts a material between two (or more) outputs from the flow switch based on the flow rate of material as it passes through the flow switch. In particular, the flow switches described herein may achieve differential flow sorting based on the differences between the resistance to flow through the outputs and different static fluid pressure at the interface between each output and the flow switch (e.g., the flow switch convergence region).

A flow switch typically operates by using at least two outlets connected to different outlet channels (e.g., a waste outlet flow path and a sample outlet flow path) exiting a convergence (e.g., intersection) region of the flow switch, where the different outlet flow paths have differential flow resistances and each outlet flow path has a different static fluid pressure. In some variations at low flow rates (e.g., flow rates below a lower threshold value) flow out of the flow switch will be through a first outlet flow path; at higher flow rates (e.g., flow rates above a higher threshold value), the flow out of the flow switch will be through a second outlet flow path. In particular, the first (e.g. "low flow") outlet flow path may have a static fluid pressure that is lower than the static fluid pressure at the second (e.g., "high flow") outlet flow path, and the resistance to fluid flow along the first outlet flow path to a first container may be higher than the resistance to fluid flow along the second outlet flow path to a second container. Thus, sorting may be achieved by changing the flow rate of fluid in the flow switch so that the material (e.g., the microparticle surrounded by the fluid) is switched from a first output to a second output.

Any of the fluidic apparatus described herein may contain both microfluidic structures and macrofluidic structures to achieve cell sorting and cell dispensing at the same time. For example, the flow resistance and/or static fluid pressures, as well as the flow rate of a fluid within the flow switch may be manipulated by microfluidic or macrofliudic structures.

In addition, any of the apparatus described herein may include features that prevent disruptions in the flow rate (e.g., preventing unintentional or uncontrolled changes in flow rate, such as turbulence) for fluid within the flow switch. Also, any of these systems may include a degasser to remove bubbles or to prevent bubble formation. Further, the flow paths through the flow switch may be configured to prevent or reduce turbulent flow.

The flow rate of a fluid entering and within the flow switch may be controlled. In any of the apparatus described, the flow rate may be induced by pressurizing the fluid. Thus any of these apparatus and method for using them may include operation of a pump (e.g., air pump) to pressurize the system and/or vacuum, and/or a pressure sensor to regulate the pressure.

The flow rate of fluid entering or within the flow switch may be modified during operation by any appropriate method. For example, the flow rate of fluid may be modified by increasing/decreasing the driving force acting on the stream of fluid entering or within the flow switch, such as by modifying the pressure, and/or by the addition of fluid to the fluid stream (often referred to herein as the sample fluid, which contains the microparticles), where the added fluid may be flowing at a different rate (e.g., faster or slower). In other variations the rate of the sample fluid within or before entering the switch may be modified by changing the geometry of a channel in which the fluid is traveling (e.g., constricting/expanding).

The apparatus described herein may also be configured so that they can be primed or prepared for operation. For example, a low liquid flow rate in microfluidic structure during system priming may be overcome by reversing the flow in the microfluidic structure and by backfilling with air which has much lower flow resistance than liquid.

Any of the devices described herein may include visualization with microscope lens coupled with a digital camera to identify microparticles having a predetermined characteristic (e.g., size, shape, fluorescence or other marker, etc.). Any of the devices described herein may include optical light collecting system to measure fluorescent light emitted from microparticles.

Any of the methods for sorting a microparticles described herein may include modifying the rate of flow (flow rate) of a fluid and/or within a flow switch that differentially directs the flow based on the flow rate. For example, a method of sorting microparticles may include: passing a sample fluid into a flow switch at a first flow rate; changing a flow rate of the sample fluid to a second flow rate when a microparticle having a predetermined characteristic is present in the flow switch; passing the sample fluid flowing through the flow switch into a waste outlet flow path when the sample fluid is traveling though the flow switch at approximately the first flow rate; and passing the sample fluid flowing through the flow switch into a sample outlet flow path when the sample fluid is traveling through the flow switch at approximately the second flow rate. The flow switch may differentially direct flow through the flow switch between a sample outlet flow path and a waste outlet flow path based on the flow rate of the sample fluid because the sample outlet flow path and the waste outlet flow path may have differential fluid properties such as different static fluid pressures and different resistances to flow. For example, the waste outlet flow path may have a static fluid pressure that is lower than a static fluid pressure in the sample outlet flow path, and the resistance to fluid flow along the waste outlet flow path to a waste container (e.g., including the waste outlet flow path and any additional waste channel) may be higher than the resistance to fluid flow along the sample outlet flow path to a sample container (e.g., including the sample outlet flow path and any additional sample channel). In any of these examples, the waste and sample outlet flow path may be switched (e.g., the sample outlet flow path may have a static fluid pressure that is lower than a static fluid pressure in the waste outlet flow path, and the resistance to fluid flow along the sample outlet flow path may be higher than the resistance to fluid flow along the waste outlet flow path).

Any of the methods and apparatus may be configured to detect a microparticle having a predetermined characteristic in the sample fluid, and further may alter the flow rate of the fluid surrounding the microparticle when the microparticle will be in the flow switch. In general, any appropriate method or device for changing the flow rate may be used. For example, changing the flow rate may include accelerating or decelerating the flow rate of the fluid by adding energy to the fluid, adding one or more agents to the fluid (e.g., viscosity modifying agents), or mechanically increasing or decreasing the flow rate. In particular, changing the flow rate of the sample fluid may include passing additional fluid to the flowing fluid, e.g., adding additional fluid into the flow switch from a second flow path to increase the flow rate of the fluid in the flow switch.

For example, a method of sorting microparticles may include: passing a microparticle surrounded by fluid into a flow switch; changing a flow rate of the fluid surrounding the microparticle from a first flow rate to a second flow rate when the microparticle has a predetermined characteristic and is present in the flow switch; and passing the microparticle through the flow switch into a waste outlet flow path when the fluid surrounding the microparticle is traveling through the flow switch at approximately the first flow rate, or passing the microparticle through the flow switch into a sample outlet flow path when the fluid surrounding the microparticle is traveling through the flow switch at approximately the second flow rate. The microparticle may be flow sorted when the static fluid pressure in the waste outlet flow path is lower than a static fluid pressure in the sample outlet flow path, and/or when the resistance to fluid flow along the waste outlet flow path is higher than the resistance to fluid flow along the sample outlet flow path (e.g., when the microparticle is traveling through the flow switch into sample channel).

Any of the methods described herein may include detecting that the microparticle has the predetermined characteristic. In general, the microparticle may be a cell (or in some variations a cluster of cells). Any appropriate (e.g., detectable, including visually detectable) predetermined characteristic may be used by an apparatus or as part of a method to increase/decrease the flow of the fluid surrounding the microparticle and thereby sort the particle. For example, the predetermined characteristic may be selected from one or more of: shape, size, and fluorescence intensity.

The flow rate of a fluid (including the fluid surrounding the microparticle, which may be referred to as sample fluid) may be set by pressurizing the fluid being sent to the flow switch. Thus, a method of sorting may include pressurizing the fluid surrounding the microparticle to a predetermined pressure or range of pressures.

In another example, a method of sorting microparticles may include: passing a microparticle surrounded by fluid from a first flow path into a flow switch at a first flow rate; increasing the flow rate of the fluid surrounding the microparticle to a second flow rate by adding fluid to the fluid surrounding the microparticle when the microparticle has a predetermined characteristic and is present in the flow switch; passing the microparticle through the flow switch into a waste outlet flow path when the fluid surrounding the microparticle is traveling through the flow switch at approximately the first flow rate, or passing the microparticle through the flow switch and into a sample outlet flow path when the fluid surrounding the microparticle is traveling through the flow switch at approximately the second flow rate; and wherein a static fluid pressure in the waste outlet flow path is lower than a static fluid pressure in the sample outlet flow path, and further wherein the resistance to fluid flow along the waste outlet flow path on the way to a waste container is higher than the resistance to fluid flow along the sample outlet flow path when the microparticle is traveling through the flow switch into sample outlet flow path on the way to a sample container (e.g., multi-well plate, culture dish, etc.). As mentioned, adding fluid may include opening a valve controlling flow through a second flow path into the flow switch.

Any of these methods may include detecting a microparticle having the predetermined characteristic in the sample fluid (e.g., a predetermined characteristic may be selected from one or more of: cell shape, cell size, and fluorescence intensity). Detecting may be performed as or before the microparticle enters the flow switch, e.g. in a first fluid path that opens into the flow switch from a source of microparticles. For example, a detector may include a sensor and/or camera and one or more lenses (microscope objectives) to magnify the image, and detection software that examines images taken from the sensor/camera to determine if there is a microparticle (e.g., cell) in the field of view in or about to enter the flow switch.

The methods and apparatus for sorting microparticles described herein may also be referred to as continuous-flow, because the stream of fluid containing the microparticles may be continuously held within the flow switch, without forming a droplet that is then deflected/sorted. This may allow more precise positioning of the sorted material, e.g., into 96 well plates, etc., as the microparticle and fluid surrounding it are deposited from a fluidic outlet of the flow switch into a target (e.g., multi-well plate).

Also described herein are microparticle sorting apparatus. An apparatus may be a device or a system. Any of the microparticle sorting apparatus described herein may include a flow switch which typically includes one or more inputs (e.g., flow lines into the flow switch), and two or more outputs (e.g., flow lines leaving the flow switch). At least one input and all of the outputs may all intersect within the flow switch in an intersection region.

For example, a microparticle sorting apparatus may include: a flow switch; a first flow path configured to pass a fluid surrounding a microparticle into the flow switch at a first flow rate; a valve regulating a second flow path, the second flow path configured to increase a flow rate of the fluid surrounding the microparticle in the flow switch to a second flow rate; a waste outlet flow path out of the flow switch; and a sample outlet flow path out of the flow switch; wherein the waste outlet flow path, sample outlet flow path and fluid switch are configured so that the waste outlet flow path has a static fluid pressure that is lower than a static fluid pressure in the sample outlet flow path, and further wherein the resistance to fluid flow along the waste outlet flow path (on the way to a waste container) is higher than the resistance to fluid flow along the sample outlet flow path (on the way to the sample container) when the microparticle is traveling through the flow switch into sample channel. Any of these microparticle sorting apparatus may also include a degasser configured to remove gas (e.g., dissolved air) from fluid entering the flow switch and/or otherwise prevent bubbles from occurring in the flow switch or connecting fluid lines.

As mentioned above, any of the fluid flow paths (lines) in the apparatus may be pressurized to drive the flow of fluid. For example, the apparatus may include an air pump configured to pressurize fluid before it enters the first flow path. Multiple air pumps may be used, or a single air pump may pressurize multiple lines. Any of these apparatus may include one or more pressure regulators configured to regulate pressure in a flow path, e.g., in the first flow path, the second flow path or both the first and second flow paths.

As mentioned above, any of these apparatus may include a detector sub-system (which may also be referred to herein as an imaging module) for detecting a microparticle having characteristic properties and triggering a change in the flow to sort the detected microparticle using the flow switch. A detection sub-system may include a sensor, such as a camera or photomultiplier tube, and/or a processor configured to process information from the camera or photomultiplier tube. The sub-system may also include one or more lenses (microscope lenses) and/or a light source configured to illuminate fluid potentially containing a microparticle. In general, the detector sub-system (e.g., imaging module) may be configured to detect a microparticle having predetermined properties. When the predetermined properties includes a fluorescence signal, the sub-system may include a fluorescent detection system.

Any of these apparatuses may include a controller configured to activate the valve and increase the flow rate of the fluid surrounding the microparticle in the flow switch when the microparticle is in the flow switch. The controller may include a timer (e.g., delay timer) configured to delay activation of the increased flow rate until the microparticle is predicted to be properly positioned in (e.g., in the intersection region of) the flow switch. In some variations the imaging sub-system may determine the rate of movement of the microparticle and thus the apparatus may calculate the delay of the timer delay, since the distance between the imaging sensor/camera of the imaging sub-system may be a known (and fixed) distance.

An appropriate valve may be used, such as a solenoid valves. As mentioned, the valve may be configured to be activated after a delay. In general, the valve is connected to a controller that determines when to open the valve and for how long to open the valve (e.g., based on the rate of motion of the microparticle and its distance from the intersection region of the flow switch).

In general, the flow rates though the flow switch may be determined in part by the geometry of the flow paths. For example, in some variations the diameter of the second flow path is greater than the diameter of the first flow path. This may allow for the addition of fluid moving at a different (e.g., faster) rate than the fluid surrounding a microparticle; thus the resulting change in the flow rate of the fluid surrounding the microparticle may allow sorting of the microparticle by the flow switch.

As mentioned above, a flow switch may include one or more inlets and two or more outlets that form a part of the flow switch, as well as an intersection region which links inlet(s) and outlets. The portions between an inlet/outlet and intersection region may be referred to as inlet/outlet flow paths, such as a first (e.g., sample) inlet flow path, second (e.g., flush) inlet flow path, first (or waste) outlet flow path, and second (or sample) outlet flow path. The flow switch may include a sample inlet that couples to a sample inlet flow path connecting to a source of sample fluid containing microparticles, a flush inlet that couples to a flush inlet flow path connecting to a source of flushing fluid, a waste outlet that couples to a waste outlet flow path connecting to a waste channel (and thereafter a waste container), and a sample outlet that couples to a sample outlet flow connecting to a sample channel that dispenses the sorted microparticle to a target portion of a sample container (e.g., multiwall plate).

For example, described herein is a microparticle sorting apparatus, the apparatus comprising: a flow switch; a first flow path into the flow switch, the first flow path configured to pass a fluid containing a microparticle at a first flow rate; a valve regulating a second flow path into the flow switch, the second flow path configured to increase the flow rate of the fluid surrounding the microparticle to a second flow rate by adding additional fluid to the fluid surrounding the microparticle; a waste flow path out of the flow switch; a sample flow path out of the flow switch, wherein the waste outlet flow path and sample outlet flow path of the fluid switch are configured so that the waste outlet flow path has a static fluid pressure that is lower than a static fluid pressure in the sample outlet flow path, and further wherein the resistance to fluid flow along the waste outlet flow path on the way to a waste container is higher than the resistance to fluid flow along the sample outlet flow path on the way to a sample container (e.g., multiwall plate), so that the sample fluid passes into the waste outlet flow path when the flow rate of the sample fluid is at the first flow rate, and the sample fluid passes into the sample outlet flow path when the flow rate of the sample fluid is at the second flow rate; an imaging module configured to detect the microparticle; and a controller configured to activate the valve and increase the flow rate of the fluid surrounding the microparticle.

Any of the apparatuses described herein may include an illumination source appropriate for identifying the microparticles by the imaging sub-system.

DETAILED DESCRIPTION

Figure 1:
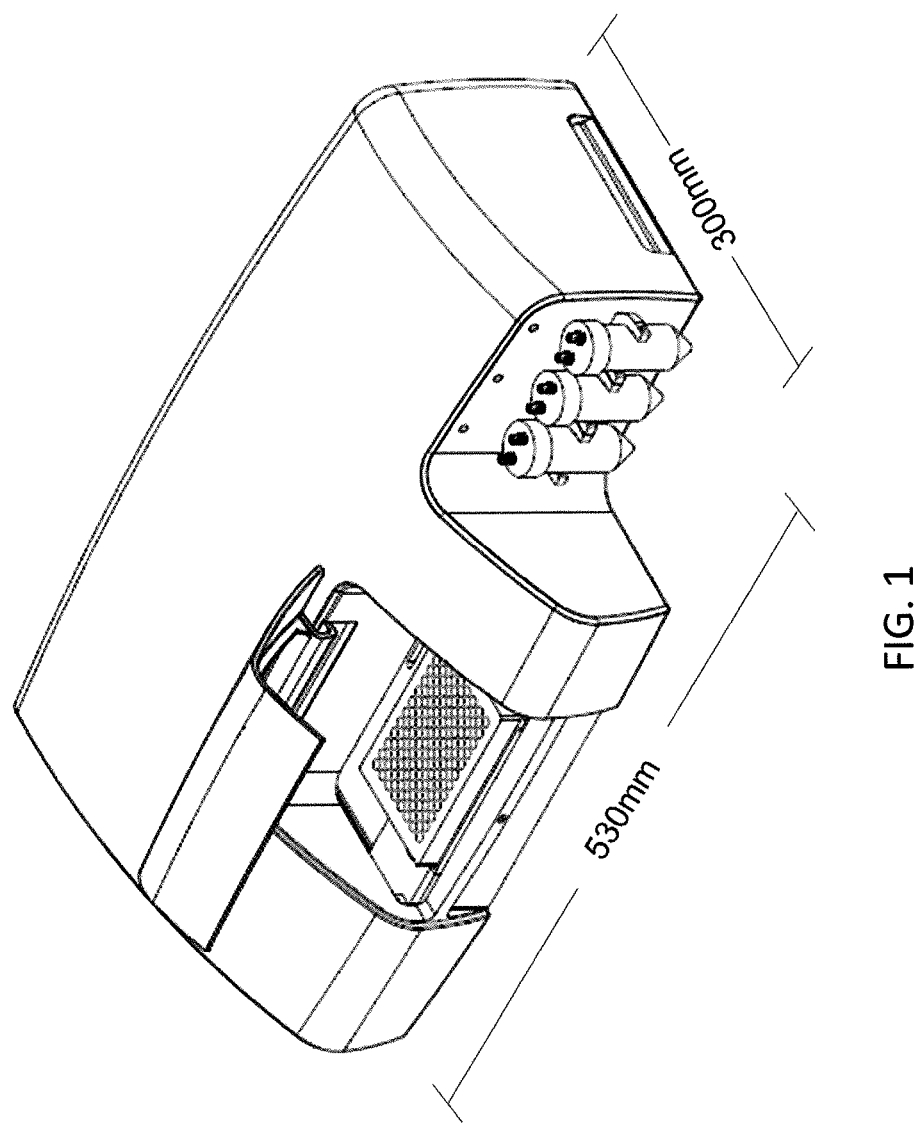
FIG. 1 shows one example of a microparticle sorting apparatus.

Described herein are apparatus and methods for sorting microparticles surrounded by fluid using a flow switch that sorts detected microparticles based on the flow rate (speed) of the fluid surrounding the microparticle.

For example, a method of sorting microparticles may include alternating fluidic flow path using a flow switch which contains at least one inlet and at least two outlets, wherein alternating fluidic flow path is achieved by changing flow rate into the flow switch system. In some variations the flow switch includes at least two inlets and at least two outlets. The method may include maintaining one flow path at low flow rate wherein the pressure in one flow outlet is kept lower than that in the other flow outlet. The flow switch may also have a lower pressure in one flow outlet as compared to the other flow outlet, for example, by lowing the opening of one flow outlet as compared to that of the other flow outlet. The other flow path may be maintained at high flow rate wherein flow resistance in one flow outlet is lower than that in the other flow outlet.

In general, the apparatus (e.g., systems and devices) described herein may be used to sort any appropriate microparticles, including microparticles that are single cells, clusters of cells, inorganic particles, or any other object, typically of small size (e.g., <1 mm, <100 µm, etc.).

The sorting may be controlled by an imaging sub-system that images the microparticles in the fluid supplied into the flow switch, which may be referred to as source fluid. The imaging sub-system may continuously or discretely monitor the source fluid before or as it flows into the flow switch to determine when a microparticle having one or more predetermined characteristics. For example, the system may be configured to sort based on cell shape, cell size, cell morphology, of a label on/applied to the cell (e.g., fluorescence intensity of a fluorescently labeled cell). Once a microparticle having the desired characteristics is identified, it may be sorted by changing the flow rate of the solution around the microparticle so that it is directed to a different outlet (e.g., a fast-flow outlet) instead of the tonic, "waste" outlet (e.g., low-flow outlet). The sample inlet into the (or within the) flow switch may be configured so that microparticles having predetermined characteristics occur discretely within the field of view of the imaging sub-system. The sample inlet channel may be adapted or configured to permit only single microparticles though at a time, for example, by including a narrow channel region, and particularly the region being viewed by the imaging sub-assembly. Alternatively or additionally, the sample fluid containing the microparticles may be diluted such that the occurrence of microparticles within the field of view is relatively uncommon (e.g., probabilistically low).

As mentioned, one or more inlet fluidic paths formed as part of the flow switch may be microfluidic channels. Fluid (sample fluid) may be driven within the flow path at a rate that is determined, in part, by a pressure, e.g., air pressure provided by an air pump. The system may include feedback regulating the fluid pressure within the different regions of the flow switch, including in particular the source fluid input to the flow switch.

In general, differential switching based on fluid flow rate may be achieved within the flow switch by including one outlet fluidic path that has a fluidic resistance that is lower than the fluidic resistance of the rest of outlet fluidic paths. In addition the static water pressure at the region of the outlet flow path near the intersection region of the flow switch, e.g., immediately after entering an outlet pathway, may be different. For example, one outlet may have an opening (connecting to a container such as a waste container or a sample container) that is lower than the opening of the other outlet(s), resulting in a different static water pressure between the outlets of flow switch.

In general, the flow switches described herein may be made of any appropriate material, including glass, polycarbonate, a combination of both, or from some other material. In general, the inlet (sample inlet) to a flow switch may have a cross section area between 100 µm$^2$ and 100,000 µm$^2$. The other inlet has cross section area between 1000 µm$^2$ and 1,000,000 µm$^2$.

An inlet or outlet of the apparatus described may have a round, oval, triangular, rectangle, or other shaped cross section. For example, an inlet may have an internal dimension of 30 µm×300 µm (H×W); the other inlet may have a circular cross section with internal diameter of 400 µm. In this example, two outlets have cross section area between 1000 µm$^2$ and 1,000,000 um$^2$. One outlet may have a circular cross section with internal diameter of 400 µm and the other outlet has circular cross section with internal diameter of 300 µm.

In general, any of the flow switches described herein may be manufactured from a single piece of material using a method such as polymer hot embossing. A flow switch may be manufactured in two steps. For example, one inlet with smaller cross section may be manufactured from one material. The rest of the flow switch may be manufactured from another material, and the two pieces are glued together.

Any of the apparatus for sorting microparticles such as cells described herein may be integrated into a system (such as a bench top or desktop system) that may automatically and efficiently sort a source of microparticles. For example, FIG. 1 shows a desk top device which is able to sort cells directly into a 96-well cell culture plate. In this example, the system includes a flow switch that is built into the overall system. The system also include an air pump for pressurizing the fluids (source fluid, flushing fluid) as well as sensors (pressure regulators), a vacuum source (for priming/clearing the system between or after operation), a valve for open/closing a line to increase and/or decrease the flow rate of the microparticle through the flow switch) and at least part of the imaging sub-system (e.g., light source, lenses, camera, photomultiplier tube etc.). These elements are illustrated in greater detail in FIG. 2. In FIG. 1 the overall system may be enclosed in a housing, as shown. The housing and system may be configured to interface (by connecting directly and/or wirelessly) to a processor such as a computer, laptop, smartphone, etc. In some variations, the apparatus includes an integrated/dedicated processor, for analyzing the microparticles and deciding when to sort using the flow switch.

Figure 2:
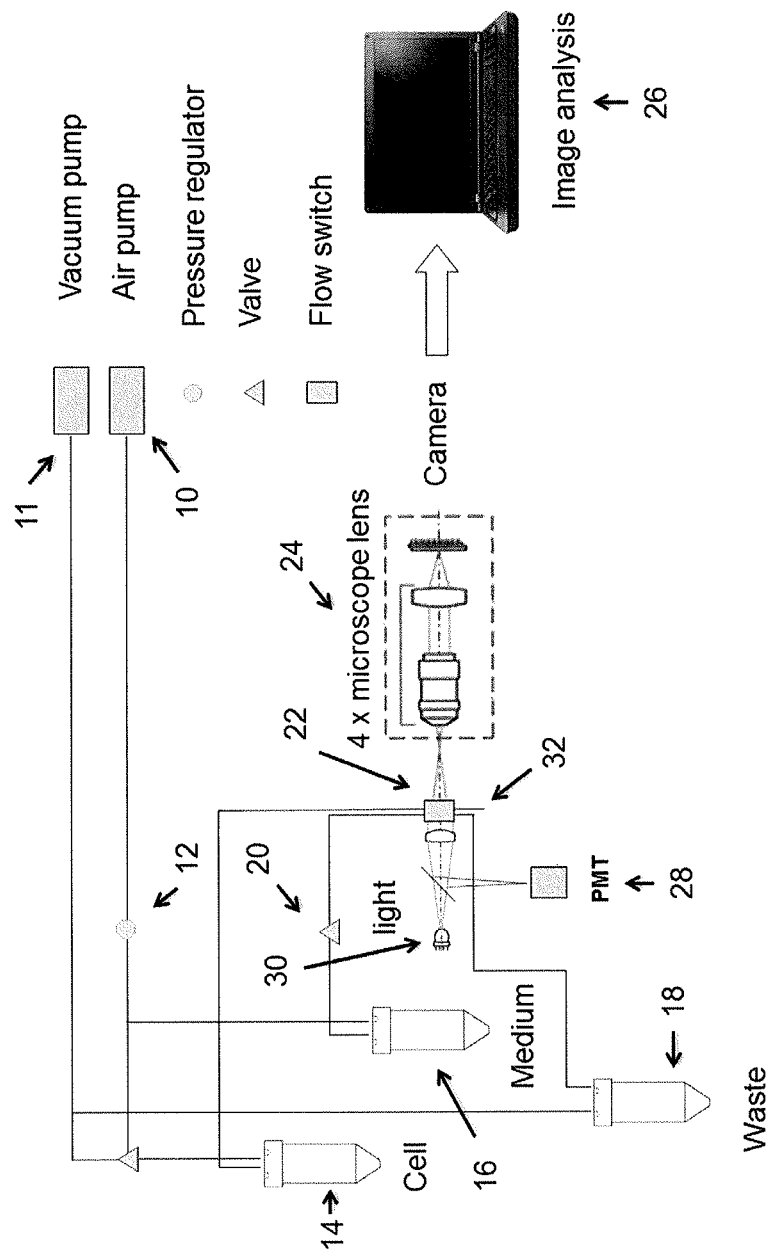
FIG. 2 schematically illustrates one variation of a microparticle sorting apparatus.

FIG. 2 shows a diagram of how sorting is achieved. In FIG. 2, microparticles, such as cells, are stored in bottle 14. Bottle 16 contains only liquid, and in the case of cell sorting, it contains cell medium or saline buffer such as phosphate buffered saline. Both bottles are pressurized by a micro-diaphragm gas pump 10. The pressure in bottle 14 and bottle 16 is regulated by pressure regulator 12. The pressure in bottle 14 and bottle 16 may be 0-30 psi. In one embodiment, the pressure in bottle 14 and bottle 16 is 2 psi. Bottle 14 is directly connected to one inlet of the flow switch 22 through silicone tube. When bottle 14 is pressurized, liquid in bottle 14 will constantly flow through silicone tube into flow switch 22. Bottle 16 is connected to the other inlet of flow switch 22 through silicone tube. The flow of liquid from bottle 16 to flow switch 22 is controlled by solenoid valve 20. When cells are flowed through the flow switch 22, they are visualized through camera coupled with microscope lens 24. The fluorescence intensity of the cell is measured by photomultiplier tube (PMT) 28 at the same time. If the cell does not meet the preset criteria, such as the size, shape and fluorescence intensity, solenoid valve 20 remains closed. The cell will flow out of flow switch into waste bottle 18. If the cell meets the preset criteria, solenoid valve 20 opens for short period of time. Medium will flow into flow switch 22. The majority of medium will flow out of sample channel 32. The flow of medium will carry the targeted cell out of the nozzle of the sample channel 32. Thus sorting and dispensing a single cell is achieved at the same time.

Successful sorting and dispensing cells in this invention may depend on the unique design of flow switch. Referring to the schematic illustration of FIG. 3A, in this example a flow switch has two flow inlets 34 and 38, connected to inlet flow paths 40 and 42, respectively, and two flow outlets 32 and 36, connected to the flow outlet paths 46 and 44, respectively, of the flow switch. The inlet and outlet flow paths all converge in a common convergence region 58. Inlet 34 is connected to bottle 14 and inlet 38 is connected to bottle 16. Microparticles flow into flow switch through a sample inlet flow path 40.

Additional fluid flows through a flush inlet flow path 42 to alter the flow rate of fluid surrounding the microparticles in the flow switch from low flow rate to high flow rate. Outlet 32 is connected to sample channel 51 and outlet 36 is connected to waste channel 53 which leads to the waste container (bottle) 18. The flow switch contains both microfluidic flow channels and macrofluidic flow channels. Sample inlet flow path 40 is a microfluidic channel. Flush inlet flow path 42, waste outlet flow path 44 and sample outlet flow path 46 are macrofluidic channels. In one embodiment, sample inlet flow path 40 is made of glass capillary with rectangle cross-section with the dimension 30 μm×300 μm (H×W). In one embodiment, flush inlet flow path 42, waste outlet flow path 44 and sample outlet flow path 46 are made from a single piece of polycarbonate. The cross-sections of flush inlet flow path 42, waste outlet flow path 44 and sample outlet flow path 46 may be circular. In one embodiment, the diameters of flush inlet flow path 42 and sample outlet flow path 46 are 400 μm. The diameter of waste outlet flow path 44 is 300 μm. Sample inlet flow path 40, flush inlet flow path 42, waste outlet flow path 44 and sample outlet flow path 46 are converged at the center of flow switch 58.

Figure 3B:
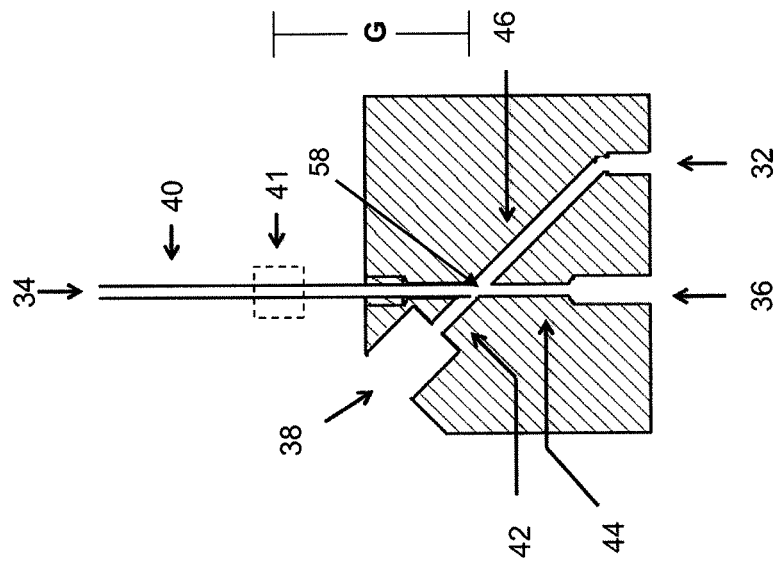
FIG. 3B is a cross-section through a flow switch such as the one shown in FIG. 3A.
Figure 3A:
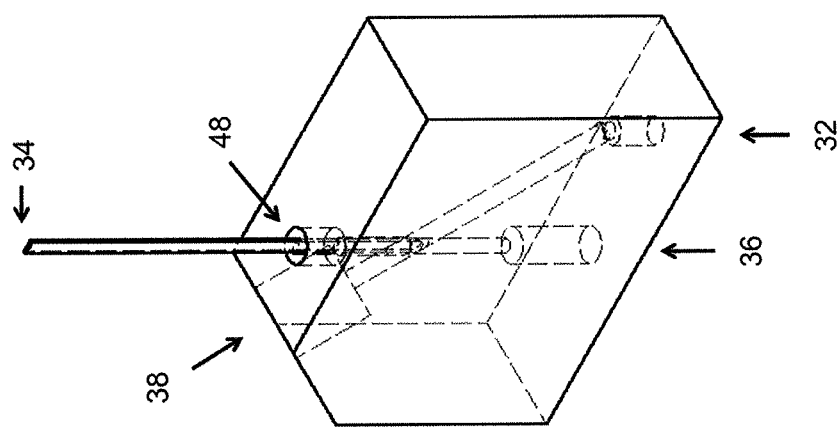
FIG. 3A illustrates one embodiment of flow switch.
Figure 4:
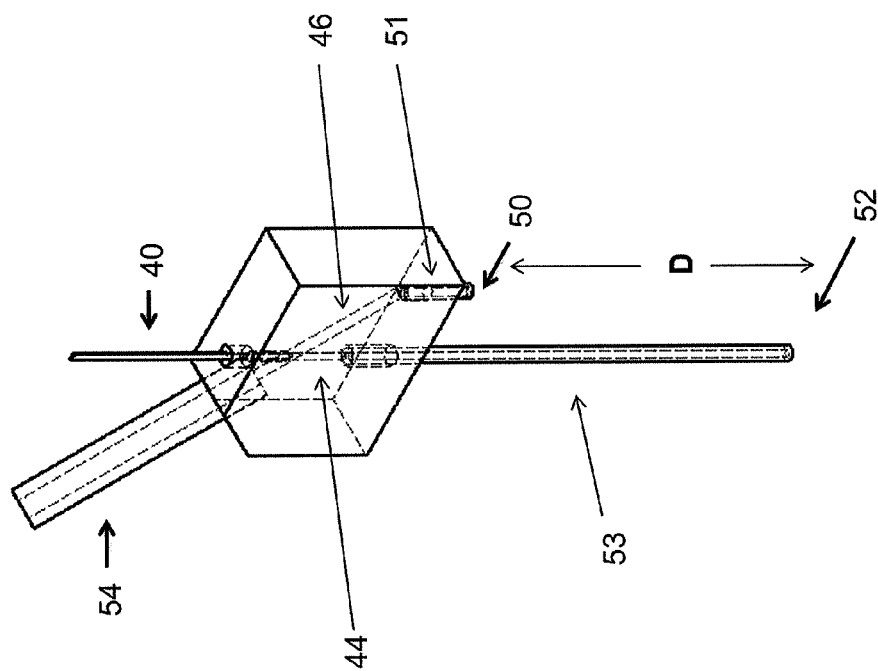
FIG. 4 shows an embodiment of flow switch assembly with source, waste and dispensing channels (tubes) shown attached. In some variations these attached channels may be integrated into the flow switch.

To achieve cell sorting, there must be as least two flow outlets: one for wanted (sample) cells and the other for unwanted (waste) cells. An easy way to change flow path between two flow outlets is to change the flow resistance between two flow outlets through valves. For example, there are valves A and B in the flow path A and B respectively. To let the liquid to flow only through flow path A, and not path B, simply turn valve A in the path A on and turn valve B in the path B off. However having two controllable valves in two flow path outlets creates large dead volume. This is why such a method is rarely used in cell sorting apparatus. Traditionally, cell sorting was achieved by keeping both flow outlet paths open and by applying certain amount of external physical forces, such as mechanical force, acoustic force, hydraulic force, optical forces, magnetic force, dielectrophoretic force, or electrostatic force as described in the background section, directly to a targeted cell to force it to move from one flow path to the other flow path. In contrast, in the flow switches described herein, both flow outlet paths are open (FIG. 4), and no external force is used to switch flow paths. Switching between two flow paths may be achieved by simply changing flow rate into the flow switch. In FIG. 4, cells flow into flow switch through sample inlet flow path 40. When medium flow into flow switch through silicone tube 54 is blocked by valve 20, cell flow is the only flow into the flow switch. Normally cells can flow out of the two outlets of flow switch through either waste outlet flow path 44 or sample outlet flow path 46. However, the flow switch is assembled in such way that the waste channel opening 52 is below the sample channel opening 50. The distance between the waste channel opening 52 and the sample channel opening 51 is D in FIG. 4. In one embodiment, D equals 70 mm. The flow rate of cell through microfluidic channel 40 is low. In one embodiment, the cell flow rate is 20 μm/min. Because cross-section area of the waste channel 53 is much larger than the cross-section area of sample inlet flow path 40, the pressure drop created by cells flowing through waste channel 53 is typically smaller than the static water pressure D in FIG. 4. Therefore, cells only flow into waste outlet flow path 44 and finally into waste. No cells will flow into sample outlet flow path 46 and out of sample channel 51. While cells are flowed through the sample inlet flow path 40, they are inspected by a digital high speed camera and their fluorescence intensities are measured by PMT through an inspection window 41 (FIG. 3B). If the cell meets the preset criteria, such as size, shape and fluorescence inten-sity, valve 20 opens after a certain amount of delay, and medium flows into flow switch through silicone tube 54. The flow rate of medium into the flow switch is much larger than that of cell flow. In one embodiment, the medium flow rate is 500 ul/min. The diameter of silicone tube 54 is larger than that of the waste channel 53. In one embodiment, the diameter of silicone tube 54 is 0.762 mm whereas the diameter of silicone tube 52 is 0.30 mm. The large flow through silicone tube 54 into flow switch will change the flow pattern. A majority of medium will flow into sample outlet flow path 46 and out of sample channel 51 because flow resistance through the sample channel 51 is lower than that through waste channel 53. Movement of medium into sample outlet flow path 46 will also move targeted cell into sample outlet flow path 46 and out of the sample channel 51. Valve 20 only opens long enough so that the targeted could be dispensed out of the sample channel 51. In one embodiment, valve 20 opens for 25 ms. Thus single cell sorting and dispensing is achieved by changing the flow rate in the flow switch from 20 ul/min to 520 ul/min. Because target cell is dispensed out of the flow switch as a droplet through the sample channel 51, the location of dispensed droplet can be precisely controlled to accuracy less than 1 mm.

When valve 20 is closed, the pressure in waste outlet flow path 44 in FIG. 4 is lower than that in sample outlet flow path 46 because the opening 52 of waste channel 53 is lower than the opening 50 of sample channel 51. Lower pressure in waste outlet flow path 44 as compared to sample outlet flow path 46 may also be achieved by connecting the waste bottle 18 to a vacuum pump without setting opening of waste channel 53 to be lower than the opening of sample channel 51.

Figure 5:
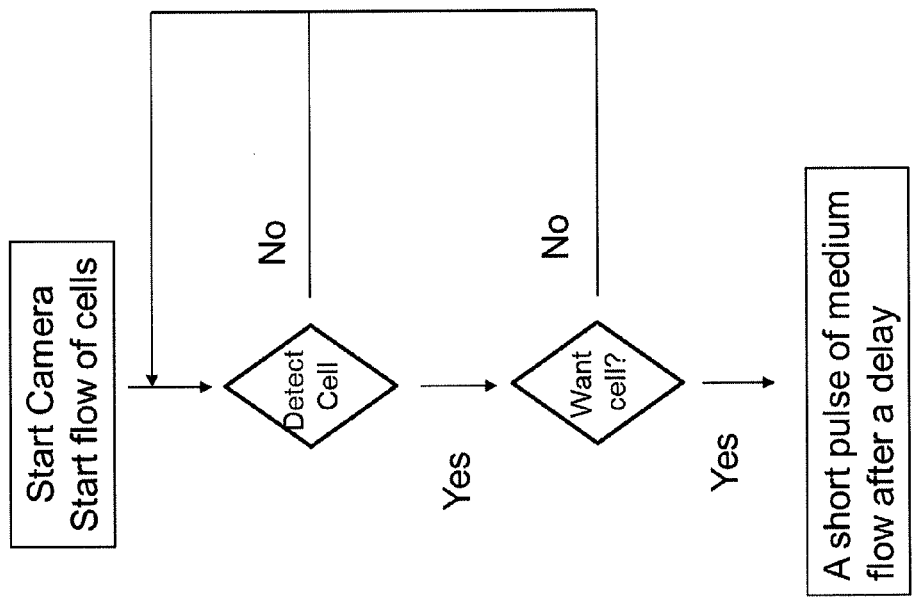
FIG. 5 is a flowchart showing how a fluidic system for sorting microparticles may be controlled.

FIG. 5 is the flowchart of one variation of a machine vision system. In this embodiment (sub-system), cells are sorted by the apparatus. A computer controls the flow of medium via solenoid valve 20. After the fluidic system has been primed and filled with liquid, the computer starts image capture through the camera and sets solenoid valve 20 at close state. If the computer detects a single cell, it determines if the cell meets the pre-set condition. If the cell meets such condition, the computer may open solenoid 20 for short period of time after a certain amount of delay to dispense selected cell. In one embodiment, computer opens solenoid valve 20 for 25 ms to dispense the selected cell. The machine vision system not only detects each individual cell, but also determine the speed of each individual cell travelling in the sample inlet flow path 40 (FIG. 3B). The distance between inspection window 41 and the converging point of flow paths 58 is G. Delay time=G/cell speed−system latency. There are several factors contributing to system latency. 1). It takes time for camera to capture cell image and to transfer from the camera to the computer. 2). It takes time for the computer to identify cell in each image sent from the camera. 3). It takes time for the computer to send out signal to solenoid valve control citrus. 4). It takes time for solenoid valve to transit from closed state to open state. In one embodiment, cell speed is 24 mm/s, G=4 mm and system latency is 22 ms. Therefore, delay time is 145 ms. Timing of valve opening may be critical. Solenoid valve 20 should be opened at the time when the targeted cell is just about to reach the converging point of flow paths 58.

This simple flow switch may provide an effective way to sort cells. However, these flow switches may be sensitive to bubbles in the flow switch. A bubble in waste outlet flow path 44 may increase the static pressure in waste outlet flow path 44. Normal flow of unwanted cells into waste outlet flow path 44 will be diverted to sample outlet flow path 46 and out of the sample channel 51. This will dramatically decrease sorting accuracy. Because the flow of medium is pushed by pressurized air, there is high amount of dissolved air in the medium. When the valve 20 is open and medium is flow out of sample channel 51, decompression of the medium may induce the release of dissolved air in the medium and create air bubble in the flow switch. In order to sorted cell accurately, dissolved air in the medium may be removed before medium is flowed into flow switch. One way to achieve this is to add a degasser.

Using differential static pressure between two outlets of the flow switch and using differential flow resistance between the waste outlet flow path on the way to a waste container and the sample outlet flow path on the way to a sample container, a simple method of cell sorting and dispensing is achieved without complex fluidic system. The rate of cell sorting can reach 100 cells per second. Although it is much lower than the current commercial cell sorter which can sort thousands of cells per second, it is more accurate to dispense single cell to a given location because it generates larger droplets from its nozzle and the velocity of droplets leaving nozzle is lower. Because of its simple design, the instrument can be fully automated and requires no extensive training to operate. The instrument may be very useful for cell line development, monoclonal antibody selection and single cell research, such as stem cell research, single cell gene expression profiling, single cell mutation analysis, etc.

Cell sorting and dispensing may be achieved by changing flow rate into the flow switch. Flow rate of cells may be keep at a very low level. Although very low flow rates in the sample inlet flow path 40 during cell sorting may be useful for the performance of the instrument, it may become an issue during system priming if there is liquid present in the sample inlet flow path 40. In this case, it may take very long time for cells in bottle 14 to reach the sample inlet flow path 40 because the volume in the silicone tube connecting bottle 14 and sample inlet flow path 40 is much larger than the volume of the sample inlet flow path 40. To overcome the very low liquid flow rate in the sample inlet flow path 40, the flow in the sample inlet flow path 40 may be reversed using a vacuum pump 11 (FIG. 2) and backfilled with air which has much lower flow resistance than liquid. As long as the sample inlet flow path 40 and the silicone tube connecting bottle 14 and sample inlet flow path 40 are filled with air, moving cells from bottle 14 to the sample inlet flow path 40 can be achieved very quickly even with pressure in bottle 14 as low as 1 psi.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements, these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all subranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived therefrom, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of sorting and dispensing microparticles, comprising:
    passing a microparticle surrounded by fluid into a flow switch;
    changing a flow rate of the fluid surrounding the microparticle from a first flow rate to a second flow rate when the microparticle has a predetermined characteristic and is present in the flow switch; and
    passing the microparticle through the flow switch into a waste outlet flow path when the fluid surrounding the microparticle is traveling through the flow switch at approximately the first flow rate, or
    passing the microparticle through the flow switch into a sample outlet flow path and dispensing the microparticle as a droplet out of the sample outlet flow path when the fluid surrounding the microparticle is traveling through the flow switch at approximately the second flow rate,
    wherein a static fluid pressure in the waste outlet flow path is lower than a static fluid pressure in the sample outlet flow path.

2. The method of claim 1, wherein the resistance to fluid flow along the waste outlet flow path to a waste container is higher than the resistance to fluid flow along the sample outlet flow path to a sample container.

3. The method of claim 1, further comprising detecting that the microparticle has the predetermined characteristic.

4. The method of claim 1, wherein changing the flow rate of the fluid surrounding the microparticle comprises adding or subtracting fluid surrounding the microparticle.

5. The method of claim 1, wherein the microparticle is a cell.

6. The method of claim 1, further comprising detecting that the microparticle has the predetermined characteristic, wherein the predetermined characteristic is selected from one or more of: shape, size, and fluorescence intensity.

7. The method of claim 1, further comprising pressurizing the fluid surrounding the microparticle to a predetermined pressure or range of pressures.

8. The method of claim 1, further comprising degassing fluid before it enters the flow switch.

9. A method of sorting and dispensing microparticles, comprising:
    passing a microparticle surrounded by fluid from a first flow path into a flow switch at a first flow rate;
    increasing the flow rate of the fluid surrounding the microparticle to a second flow rate by adding fluid that is traveling at a flow rate that is faster than the first flow rate to the fluid surrounding the microparticle when the microparticle has a predetermined characteristic and is present in the flow switch;
    passing the microparticle through the flow switch into a waste outlet flow path when the fluid surrounding the microparticle is traveling through the flow switch at approximately the first flow rate, or
    passing the microparticle through the flow switch and into a sample outlet flow path and dispensing the microparticle as a droplet out of the sample outlet flow path when the fluid surrounding the microparticle is traveling through the flow switch at approximately the second flow rate; and
    wherein a static fluid pressure in the waste outlet flow path is lower than a static fluid pressure in the sample flow path, and further wherein the resistance to fluid flow along the waste outlet flow path to a waste container is higher than the resistance to fluid flow along the sample outlet flow path to a sample container.

10. The method of claim 9, wherein adding fluid comprises opening a valve controlling flow through a second flow path into the flow switch.

11. The method of claim 9, wherein the microparticles are cells.

12. The method of claim 9, further comprising detecting the microparticle having the predetermined characteristic in the sample fluid, wherein the predetermined characteristic is selected from one or more of: cell shape, cell size, and fluorescence intensity.

13. The method of claim 9, wherein passing the sample fluid from the first flow path into the flow switch comprises passing a continuous stream of sample fluid into the flow switch.

14. The method of claim 9, further comprising pressurizing the sample fluid to a predetermined pressure or range of pressures.

15. The method of claim 9, further comprising degassing a fluid before the fluid enters the flow switch, wherein the fluid is the sample fluid, the additional fluid or both the sample fluid and additional fluid.

16. A microparticle sorting and dispensing apparatus including a flow switch, the apparatus comprising:
    a first flow path configured to pass a fluid surrounding a microparticle into the flow switch at a first flow rate;
    a valve regulating a second flow path, the second flow path configured to increase a flow rate of the fluid surrounding the microparticle in the flow switch to a second flow rate;
    a waste outlet flow path within the flow switch; and
    a sample outlet flow path within the flow switch configured to dispense droplets;
    wherein the waste outlet flow path, sample outlet flow path of the fluid switch are configured so that a static fluid pressure in the waste flow path is lower than a static fluid pressure in the sample flow path, and further wherein a resistance to fluid flow along the waste flow path to a waste container is higher than a resistance to fluid flow along the sample flow path to a sample container when the sample fluid is traveling through the flow switch into sample flow path.

17. The apparatus of claim 16, further comprising a degasser configured to remove dissolved air from fluid entering the flow switch.

18. The apparatus of claim 16, further comprising an air pump configured to pressurize fluid before it enters the first flow path.

19. The apparatus of claim 16, further comprising a pressure regulator configured to regulate pressure in the first flow path, the second flow path or both the first and second flow paths.

20. The apparatus of claim 16, further comprising an imaging module configured to detect the microparticle.

21. The apparatus of claim 16, further comprising a controller configured to activate the valve and increase the flow rate of the fluid surrounding the microparticle in the flow switch when the microparticle is in the flow switch.

22. The apparatus of claim 16, wherein the diameter of the second flow path is greater than the diameter of the first flow path.

23. The apparatus of claim 16, wherein the flow switch comprises a sample inlet coupled to the first flow path, a flush inlet coupled to the second flow path, a waste outlet coupled to the waste outlet flow path, a sample outlet coupled to the sample outlet flow path, and a convergence region wherein the first flow path, second flow path, waste outlet flow path and sample outlet flow path all converge at the convergence region.

24. A microparticle sorting and dispensing apparatus, the apparatus comprising:
- a flow switch comprising a first inlet flow path, a second inlet flow path, a waste outlet flow path, and a sample outlet flow path, wherein the sample outlet flow path is configured to dispense droplets;
- a first flow path into the first inlet flow path, the first flow path configured to pass a sample fluid containing a microparticle at a first flow rate;
- a valve regulating a second flow path into the second inlet flow path, the second flow path configured to increase the flow rate of the fluid surrounding the microparticle to a second flow rate by adding additional fluid to the fluid surrounding the microparticle;
- wherein the waste outlet flow path and sample outlet flow path of the fluid switch are configured so that the waste outlet flow switch has a static fluid pressure that is lower than a static fluid pressure in the sample outlet flow path, and further wherein a resistance to fluid flow along the waste outlet flow path to a waste container is higher than a resistance to fluid flow along the sample outlet flow path to a sample container, so that the sample fluid passes into the waste outlet flow path when the flow rate of the sample fluid is at the first flow rate, and the sample fluid passes into the sample outlet flow path to be dispensed as a droplet when the flow rate of the sample fluid is at the second flow rate;
- an imaging module configured to detect the microparticle; and
- a controller configured to activate the valve and increase the flow rate of the fluid surrounding the microparticle.

25. The apparatus of claim 24, further comprising a degasser configured to remove dissolved air from fluid entering the flow switch.

26. The apparatus of claim 24, further comprising an air pump configured to pressurize fluid before it enters the first flow path.

27. The apparatus of claim 24, further comprising a pressure regulator configured to regulate pressure in the first flow path.

28. The apparatus of claim 24, wherein the diameter of the second flow path is greater than the diameter of the first flow path.

29. The apparatus of claim 24, wherein the flow switch comprises a converging region wherein the first inlet flow path, the second inlet flow path, the waste outlet flow path and the sample outlet flow path all converge.

30. The apparatus of claim 1, wherein both the waste outlet flow path and the sample outlet flow paths are open.

* * * * *